US008409642B2

(12) United States Patent
Nsereko et al.

(10) Patent No.: US 8,409,642 B2
(45) Date of Patent: Apr. 2, 2013

(54) FERULATE ESTERASE-PRODUCING BACTERIAL STRAIN FOR ENHANCING PLANT FIBER DIGESTION IN AN ANIMAL

(75) Inventors: Victor Nsereko, Johnston, IA (US); William Rutherford, Des Moines, IA (US); Brenda Smiley, Granger, IA (US); Annette Spielbauer, Ankeny, IA (US)

(73) Assignee: Pioneer Hi-Bred International, Inc., Johnston, IA (US)

( * ) Notice: Subject to any disclaimer, the term of this patent is extended or adjusted under 35 U.S.C. 154(b) by 883 days.

(21) Appl. No.: 12/233,013

(22) Filed: Sep. 18, 2008

(65) Prior Publication Data

US 2009/0010903 A1 Jan. 8, 2009

Related U.S. Application Data

(62) Division of application No. 11/217,764, filed on Sep. 1, 2005, now Pat. No. 7,799,551.

(60) Provisional application No. 60/606,389, filed on Sep. 1, 2004.

(51) Int. Cl.
*C12P 21/04* (2006.01)
*C12P 1/04* (2006.01)
*C12N 1/20* (2006.01)
*A01N 63/00* (2006.01)
*A23C 9/12* (2006.01)
*A23B 7/10* (2006.01)

(52) U.S. Cl. ...... 426/54; 435/170; 435/252.9; 435/71.1; 424/93.45; 426/61

(58) Field of Classification Search .................. None
See application file for complete search history.

(56) References Cited

U.S. PATENT DOCUMENTS

| | | | |
|---|---|---|---|
| 4,820,531 A | 4/1989 | Tomes | |
| 4,842,871 A | 6/1989 | Hill | |
| 4,863,747 A | 9/1989 | Tomes | |
| 4,981,705 A | 1/1991 | Tomes | |
| 5,026,647 A | 6/1991 | Tomes et al. | |
| 5,292,657 A | 3/1994 | Rutherford et al. | |
| 5,725,853 A | 3/1998 | Dennis et al. | |
| 5,747,020 A | 5/1998 | Rutherford et al. | |
| 6,054,148 A * | 4/2000 | Rust et al. ........................ | 426/2 |
| 6,143,543 A | 11/2000 | Michelsen et al. | |
| 6,326,037 B1 | 12/2001 | Mann et al. | |
| 6,337,068 B1 | 1/2002 | Hendrick et al. | |
| 6,403,084 B1 | 6/2002 | Chan et al. | |
| 6,489,158 B1 | 12/2002 | Hendrick et al. | |
| 6,602,700 B1 * | 8/2003 | Li et al. ........................ | 435/267 |
| 6,699,514 B2 | 3/2004 | Mann | |
| 6,750,051 B2 | 6/2004 | Tricarico et al. | |
| 7,132,589 B2 | 11/2006 | Dunn-Coleman et al. | |
| 7,453,023 B2 | 11/2008 | Dunn-Coleman et al. | |
| 7,799,551 B2 | 9/2010 | Nsereko et al. | |
| 7,919,683 B2 * | 4/2011 | Smiley et al. ............... | 800/288 |
| 2003/0024009 A1 | 1/2003 | Dunn-Coleman et al. | |
| 2004/0247568 A1 | 12/2004 | Guerino et al. | |
| 2006/0005270 A1 | 1/2006 | Dunn-Coleman et al. | |
| 2006/0046292 A1 | 3/2006 | Nsereko et al. | |
| 2008/0138461 A1 | 6/2008 | Chan et al. | |
| 2008/0138462 A1 | 6/2008 | Chan et al. | |
| 2008/0138463 A1 | 6/2008 | Chan et al. | |
| 2009/0011085 A1 | 1/2009 | Nsereko et al. | |
| 2009/0028991 A1 | 1/2009 | Chan et al. | |
| 2009/0028992 A1 | 1/2009 | Chan et al. | |
| 2009/0028993 A1 | 1/2009 | Chan et al. | |
| 2009/0162913 A1 | 6/2009 | Ruser et al. | |
| 2011/0154533 A1 | 6/2011 | Smiley et al. | |

FOREIGN PATENT DOCUMENTS

| | | |
|---|---|---|
| EP | 0 880 323 | 6/2001 |
| WO | WO 92/10945 | 7/1992 |
| WO | WO 93/13786 | 7/1993 |
| WO | WO 96/17525 | 6/1996 |
| WO | WO 00/00040 A1 | 1/2000 |
| WO | WO 02/39825 A2 | 5/2002 |
| WO | WO 02/068666 | 9/2002 |
| WO | WO 03/043411 | 5/2003 |
| WO | WO 2006/007395 | 1/2006 |
| WO | WO 2006/026763 A1 | 3/2006 |

OTHER PUBLICATIONS

Wang et al., Appl. Environmen. Microbiol. 70:2367-2372, 2004.*
Hill et al., Animal Feed Sci. Technol. 89:83-96, 2001.*
Nsereko et al., Animal Feed Sci. Technol. 145:122-135, 2008.*
Donaghy, et al., Detection of ferulic acid esterase production by *Bacillus* spp. and *lactobacilli*, Appl. Microbiol. Biotech., (1998), 50:257-260.
Erasmus, et al., Effect of Yeast Culture Supplement on Production, Rumen Fermentation, and Duodenal Nitrogen Flow in Dairy Cows, J. Dairy Sci., (1992), 75: 3056-3065.
Oba, et al., Effects of Brown Midrib 3 Mutation in Corn Silage on Dry Matter Intake and Productivity of High Yielding Dairy Cows, J. Dairy Sci., (1999), 82:135-142.
Wohlt, et al., Effect of Yeast on Feed Intake and Performance of Cows Fed Diets Based on Corn Stage During Early Lactation, J. Dairy Sci., (1998), 81: 1345-1352.
Faulds, et al., Purification and characterization of a ferulic acid esterase (FAE-III) from *Aspergillus niger*: specificity for the phenolic moiety and binding to microcrystalline cellulose, Microbiology (1994), 140:779-787.
Crepin, et al., A non-modular type B feruloyl esterase from *Neurospora crassa* exhibits concentration-dependent substrate inhibition, Biochem. J., (2003), 370:417-427.
Adesogan, A.T., "Improving Forage Quality and Animal Performance with Fibrolytic Enzymes," *Florida Ruminant Nutrition Symposium*, 2005, pp. 91-109.
Collins, M.D., et al., "Deoxyribonucleic Acid Homology Studies of *Lactobacillus casei, Lactobacillus paracasei* sp. nov., subsp. *paracasei* and subsp. *tolerans*, and *Lactobacillus rhamnosus* sp. nov., comb. nov.," *International Journal of Systematic Bacteriology*, 1989, vol. 39(2), pp. 105-108.
Driehuis, F., et al., "Fermentation Characteristics and Aerobic Stability of Grass Silage Inoculated with *Lactobacillus buchneri*, With or Without Homofermentative Lactic Acid Bacteria," *Grass and Forage Science*, 2001, pp. 330-343, vol. 56.

(Continued)

*Primary Examiner* — David J Steadman
(74) *Attorney, Agent, or Firm* — Alston & Bird LLP

(57) ABSTRACT

Ferulate esterase producing bacterial strains or functional mutants thereof and methods of using ferulate esterase producing bacterial strains as forage additives are disclosed.

9 Claims, No Drawings

OTHER PUBLICATIONS

Filya, I., "The Effect of *Lactobacillus buchneri* and *Lactobacillus plantarum* on the Fermentation, Aerobic Stability, and Ruminal Degradability of Low Dry Matter Corn and Sorghum Silages," *J. Dairy Sci.*, 2003, pp. 3575-3581, vol. 86.

Holzer, M., et al., "The Role of *Lactobacillus buchneri* in Forage Preservation," *Trends in Biotechnology*, 2003, pp. 282-287, vol. 21(6).

Jarvis, A., et al., "Improvement of a Grass-Clover Silage-Fed Biogas Process by the Addition of Cobalt," *Biomass and Bioenergy*, 1997, pp. 453-460. vol. 12(6).

Kleinschmit, D.H., and L. Kung, "A Meta-Analysis of the Effects of *Lactobacillus buchneri* on the Fermentation and Aerobic Stability of Corn and Grass and Small-Grain Silages," *J. Dairy Sci.*, 2006, pp. 4005-4013, vol. 89(10).

Loc, N.T., et al., "Cassava Root Silage for Crossbred Pigs Under Village Conditions in Central Vietnam," *Livestock Research for Rural Development*, 1997, vol. 9(2), http://www.fao.org/aga/agap/frg/feedback/lrrd/lrrd9/2/loc922.htm (12 pages, printed from Internet Nov. 17, 2009).

Moore, H.I., et al., "Silos and Silage," http://www.smallstock.info/reference/moore/silage.htm (85 pages printed from Internet Nov. 17, 2009).

Ranjit, N. K., and L. Kung, "The Effect of *Lactobacillus buchneri*, *Lactobacillus plantarum*, or a Chemical Preservative on the Fermentation and Aerobic Stability of Corn Silage," *J. Dairy Sci.*, 2000, pp. 526-535, vol. 83.

Schrag, J.D., and M. Cygler, "Lipases and $\alpha/\beta$ Hydrolase Fold," *Methods in Enzymology*, 1997, pp. 85-107, vol. 284.

Tabka, M.G., et al., "Enzymatic saccharification of wheat straw for bioethanol production by a combined cellulase xylanase and feruloyl esterase treatment," *Enzyme and Microbial Technology*, 2006, vol. 39, pp. 897-902.

Taylor, C.C., et al., "*Lactobacillus buchneri* and Enzymes Improves the Aerobic Stability of High Moisture Corn," *J. Anim. Sci.*, 2000, p. 111, vol. 78(Supp I) (Abstract 477).

Whiter A.G., et al., "The Effect of a Dry or Liquid Application of *Lactobacillus plantarum* MTD1 on the Fermentation of Alfalfa Silage,"*J. Dairy Sci.*, 2001, vol. 84, pp. 2195-2202.

* cited by examiner

FERULATE ESTERASE-PRODUCING BACTERIAL STRAIN FOR ENHANCING PLANT FIBER DIGESTION IN AN ANIMAL

CROSS REFERENCE TO RELATED APPLICATIONS

This application is a divisional of U.S. Ser. No. 11/217,764 filed Sep. 1, 2005, which claims the benefit of U.S. Provisional Application No. 60/606,389, filed on Sep. 1, 2004, which are herein incorporated by reference in their entirety.

TECHNICAL FIELD

Organisms that produce ferulate esterase and methods of using same to enhance plant fiber digestion in animals, as well as, enhance the preservation of the ensiled forage are disclosed.

BACKGROUND OF INVENTION

The plant cell wall is a complex structure consisting of different polysaccharides, the major components being cellulose, hemicelluloses and pectins. These polysaccharides may be cross-linked, or linked to lignin by phenolic acid groups such as ferulic acid. Ferulic acid may play a role in the control of cell wall growth in the plant and ferulic acid cross-linking within the cell wall is believed to restrict cell wall digestion by microorganisms (Fry et al., (1983) *Planta* 157: 111-123; and Borneman et al., (1990) *Appl. Microbial. Biotechnol.* 33: 345-351). The resistance of the plant cell wall to digestion presents significant challenges in the animal production industry. Some microorganisms are known to exhibit ferulic acid esterase activity (ferulate esterase) and thereby facilitate the breakdown of plant cell walls and fiber digestion (U.S. Pat. No. 6,143,543).

Presently, in livestock agriculture while a high-forage diet is desirable, it does not currently satisfy the demands of modern animal production. Fiber digestion is a limiting factor to dairy herd milk yield and composition, and to beef production in beef operations feeding a high forage diet, and hence restricts profitability of farmers. Enhancing fiber digestion has a dual impact: 1) the animal eats more due to a reduced gut fill and therefore produces more, and 2) the animal gets more out of what it eats since the fiber is more digestible. Ultimately, these changes should increase milk yield, in dairy cows, and beef production in forage fed animals. Farmers either have to put up with a lower level of feed digestibility and hence productivity, or they can use inoculants, forage additives or other amendments that improve the digestibility of feed.

Accordingly, farmers can treat ensiled feed or other animal feed with fiber degrading enzymes, originating mainly from molds, to improve digestibility of feed. In addition, there are several commercially available *Saccharomyces cerevisiae* yeast strains that when fed to cattle reportedly improve fiber digestion (Erasmus et al., (1992) *J. Dairy Sci.* 75: 3056-3065; and Wohlt et al., (1998) *J. Dairy Sci.* 81: 1345-1352). Another alternative approach to improving fiber digestion is the provision of a diet inherently possessing good digestibility characteristics. For corn silage, this may include brown midrib corn silage (Oba and Allen, (1999) *J. Dairy Sci.* 82: 135-142), or alternatively, corn hybrids recognized as being highly digestible. Further, new technologies incorporate fungal gene(s) responsible for the production of ferulate esterase into plant tissue for subsequent expression, resulting in improvements in fiber digestibility (WO 02/68666).

Generally, for an animal to make efficient use of the feed it consumes, the energy demands of the microorganisms in the digestive tract must be met and synchronized with the availability of plant proteins. A lack of synchrony will lead to a) proteins and other nutrients being poorly utilized in the digestive tract, b) a loss of nitrogen, in urine and feces and c) a need to feed excessive amounts of protein concentrates as supplements to the diet. The use of organisms and enzymes can improve or enhance the value of the feed animals receive and the performance of the animals. For example, WO 92/10945 discloses such a combination for use in enhancing the value of prepared silage. WO 93/13786 and WO 96/17525 relate to the enhancement of animal performance using microorganisms, while WO 93/3786 refers to a species of *Lactobacillus*. Further, it has been shown that *Lactobacillus buchneri* is suitable as a direct fed microbial to increase an animal's performance (U.S. Pat. No. 6,699,514).

SUMMARY OF THE INVENTION

It has now been found that ferulate esterase producing bacterial strains or functional mutants thereof are suitable for use as a silage inoculant for improving fiber digestibility.

Further it has been found that plant fiber digestion in an animal is enhanced by feeding the animal an effective amount of a ferulate esterase containing composition, wherein the ferulate esterase is derived from a ferulate esterase producing bacterial strain or functional mutant thereof.

Embodiments of the present invention provide methods of treating animal feed or silage with the ferulate esterase producing bacterial strains disclosed herein, as well as the treated animal feed or silage itself. Methods of improving animal performance by feeding the inoculated animal feed or silage are also provided.

DETAILED DESCRIPTION OF THE INVENTION

Before describing the embodiments of the present invention in detail, it is to be understood that the embodiments of this invention are not limited to particular compositions or methods of improving digestibility of ensiled forage, which can, of course, vary. It is also to be understood that the terminology used herein is for the purpose of describing particular embodiments only, and is not intended to be limiting.

As used in this specification and the appended claims, the singular forms "a," "an" and "the" can include plural referents unless the content clearly indicates otherwise. Thus, for example, reference to "a component" can include a combination of two or more components; reference to "feed" can include mixtures of feed, and the like.

Unless defined otherwise, all technical and scientific terms used herein have the same meaning as commonly understood by one of ordinary skill in the art to which embodiments of the invention pertain. Many methods and materials similar, modified, or equivalent to those described herein can be used in the practice of the embodiments of the present invention without undue experimentation, the preferred materials and methods are described herein. In describing and claiming the embodiments of the present invention, the following terminology will be used in accordance with the definitions set out below.

The term "digestibility," as used herein, refers to the ability to derive soluble nutrients from a feed plant material. Digestibility can be determined, e.g., by analyses that provide assay data indicating the amount of feed residue remaining in a digestion and/or by analyses that provide assay data indicating the amount of nutrients released from feed in a digestion.

The term "nutrient availability," as used herein, refers to the amount of soluble nutrients made available in a digestion. Nutrient availability can be a measure of feed digestibility. Feed plant material nutrient availability can be determined by assay of: feed plant materials, feed plant materials treated with compositions of the invention, ensiled feed plant materials, in vitro digested feed plant materials, in situ digested feed plant materials, and/or the like. Assays for measurement of nutrient availability can include, e.g., gas chromatography, sugar assays, amino acid assays, free fatty acid assays, volatile fatty acid assays, carbohydrate assays, and/or the like.

The term "inoculation," as used herein, refers to introduction of viable microbes to media or feed plant material.

The term "plant material," as used herein, refers to material of plant origin. Feed plant material can be plant material intended to be fed to an animal.

The term "conditioned media," as used herein, refers to media of the embodiments of the invention in which ferulate esterase producing bacterial species have been grown. Such media are said to be conditioned, e.g., by the release of metabolites, inhibitors, and/or enzymes into the media from the ferulate esterase producing bacterial.

Units, prefixes, and symbols may be denoted in their Si accepted form. Numeric ranges recited within the specification are inclusive of the numbers defining the range and include each integer within the defined range.

As used herein, "functional mutant" means a bacterial strain directly or indirectly obtained by genetic modification of, or using, the referenced strain(s) and retaining at least 50% of the activity of a control silage using the referenced strain. The genetic modification can be achieved through any means, such as but not limited to, chemical mutagens, ionizing radiation, transposon-based mutagenesis, or via conjugation, transduction, or transformation using the referenced strains as either the recipient or donor of genetic material.

As used herein, "isolated" means removed from a natural source such as from uninoculated silage or other plant material.

As used herein, "purified" means that a bacterial species or strain is substantially separated from, and enriched relative to: yeasts, molds, and/or other bacterial species or strains found in the source from which it was isolated.

As used herein, "animal performance" means the yield of meat, milk, eggs, offspring, or work.

The term "silage" as used herein is intended to include all types of fermented agricultural products such as grass silage, alfalfa silage, wheat silage, legume silage, sunflower silage, barley silage, whole plant corn silage (WPCS), sorghum silage, fermented grains and grass mixtures, etc.

As used herein, "pre-ensiled plant material" means grasses, maize, alfalfa and other legumes, wheat, sorghum, sunflower, barley and mixtures thereof. All of which can be treated successfully with the inoculants of the embodiments of the present invention. The inoculants of the embodiments of the present invention are also useful in treating high moisture corn (HMC).

An embodiment of the invention is a composition for use as a silage inoculant comprising a ferulate esterase producing bacterial strain or a functional mutant thereof and a suitable carrier. Suitable ferulate esterase producing bacterial strains or functional mutants thereof include *Lactobacillus* strains. Suitable ferulate esterase producing *Lactobacillus* strains or functional mutants thereof include *Lactobacillus buchneri* or functional mutant thereof, *Lactobacillus plantarum* or functional mutant thereof, *Lactobacillus brevis* or functional mutant thereof, *Lactobacillus reuteri* or functional mutant thereof, *Lactobacillus alimentarius* or functional mutant thereof, *Lactobacillus crispatus* or functional mutant thereof, and *Lactobacillus paralimentarius* or functional mutant thereof. Suitable ferulate esterase producing *Lactobacillus buchneri* or functional mutant thereof, *Lactobacillus plantarum* or functional mutant thereof, *Lactobacillus brevis* or functional mutant thereof, *Lactobacillus reuteri* or functional mutant thereof, *Lactobacillus alimentarius* or functional mutant thereof, *Lactobacillus crispatus* or functional mutant thereof, and *Lactobacillus paralimentarius* or functional mutant thereof include *Lactobacillus buchneri*, strain LN4017, deposited as Patent Deposit No. PTA-6138, *Lactobacillus plantarum*, strain LP678, deposited as Patent Deposit No. PTA-6134, *Lactobacillus plantarum*, strain LP3710, deposited as Patent Deposit No. PTA-6136, *Lactobacillus plantarum*, strain LP3779, deposited as Patent Deposit No. PTA-6137, *Lactobacillus plantarum*, strain LP7109, deposited as Patent Deposit No. PTA-6139, *Lactobacillus brevis*, strain LB1154, deposited as Patent Deposit NRRL B-30865, *Lactobacillus buchneri*, strain LN4888, deposited as Patent Deposit NRRL B-30866, *Lactobacillus reuteri*, strain LR4933, deposited as Patent Deposit NRRL B-30867, *Lactobacillus crispatus*, strain LI2127, deposited as Patent Deposit NRRL B-30868, *Lactobacillus crispatus*, strain LI2350, deposited as Patent Deposit NRRL B-30869, *Lactobacillus crispatus* strain LI2366, deposited as Patent Deposit NRRL B-30870, *Lactobacillus* species unknown, strain UL3050, deposited as Patent Deposit NRRL B-30871, and mixtures thereof.

In an embodiment of the invention the composition contains from about $10^1$ to about $10^{10}$ viable organisms of the ferulate esterase producing bacterial strain or functional mutant thereof per gram of a pre-ensiled plant material. In a further embodiment of the invention the composition contains from about $10^2$ to about $10^7$ viable organisms of the ferulate esterase producing bacterial strain or functional mutant thereof per gram of a pre-ensiled plant material. In yet a further embodiment the composition contains from about $10^3$ to about $10^6$ viable organisms of the ferulate esterase producing bacterial strain or functional mutant thereof per gram of a pre-ensiled plant material.

Suitable carriers are either liquid or solid and are well known by those skilled in the art. For example, solid carriers may be made up of calcium carbonate, starch, cellulose and combinations thereof.

An embodiment of the invention is a biologically pure culture of *Lactobacillus buchneri*, strain LN4017, having ATCC Accession No. PTA-6138. A further embodiment of the invention is a biologically pure culture of *Lactobacillus plantarum*, strain LP678, having ATCC Accession No. PTA-6134. Another embodiment of the invention is a biologically pure culture of *Lactobacillus plantarum*, strain LP3710, having ATCC Accession No. PTA-6136. An additional embodiment of the invention is a biologically pure culture of *Lactobacillus plantarum*, strain LP3779 having ATCC Accession No. PTA-6137. A further embodiment of the invention is a biologically pure culture of *Lactobacillus plantarum*, strain LP7109 having ATCC Accession No. PTA-6139. Another embodiment of the invention is a biologically pure culture of *Lactobacillus paracasei tolerans*, strain LC3200 having ATCC Accession No. PTA-6135. A further embodiment of the invention is a biologically pure culture of *Lactobacillus brevis*, strain LB1154, ARS Accession No. NRRL B-30865. Another embodiment of the invention is a biologically pure culture of *Lactobacillus buchneri*, strain LN4888, ARS Accession No. NRRL B-30866. An additional embodiment of the invention is a biologically pure culture of *Lactobacillus reuteri*, strain LR4933, ARS Accession No. NRRL B-30867.

A further embodiment of the invention is a biologically pure culture of *Lactobacillus crispatus*, strain LI2127, ARS Accession No. NRRL B-30868. Another embodiment of the invention is a biologically pure culture of *Lactobacillus crispatus*, strain LI2350, ARS Accession No. NRRL B-30869. A further embodiment of the invention is a biologically pure culture of *Lactobacillus crispatus*, strain LI2366, ARS Accession No. NRRL B-30870. Another embodiment of the invention is a biologically pure culture of *Lactobacillus* species unknown, strain UL3050, ARS Accession No. NRRL B-30871.

A deposit of the following microorganisms has been made with the American Type Culture Collection (ATCC), 10801 University Blvd., Manassas, Va. 20110-2209: *Lactobacillus buchneri* LN4017 (ATCC Accession No. PTA-6138), *Lactobacillus plantarum* LP678 (ATCC Accession No. PTA-6134), *Lactobacillus plantarum* LP3710 (ATCC Accession No. PTA-6136), *Lactobacillus plantarum* LP3779 (ATCC Accession No. PTA-6137), *Lactobacillus plantarum* LP7109 (ATCC Accession No. PTA-6139), and *Lactobacillus paracasei tolerans* LC3200 (ATTC Accession No. PTA-6135). These organisms were deposited on Aug. 3, 2004. The microorganisms deposited with the ATCC were taken from the same deposit maintained at Pioneer Hi-Bred International, Inc. (Des Moines, Iowa). Applicant(s) will meet all the requirements of 37 C.F.R. §§1.801-1.809, including providing an indication of the viability of the sample when the deposit is made. Each deposit will be maintained without restriction in the ATCC Depository, which is a public depository, for a period of 30 years, or 5 years after the most recent request, or for the enforceable life of the patent, whichever is longer, and will be replaced if it ever becomes nonviable during that period. These deposits will be maintained under the terms of the Budapest Treaty on the International Recognition of the Deposit of Microorganisms for the Purposes of Patent Procedure. During the pendency of this application, access to these deposits will be afforded to the Commissioner of Patents and Trademarks upon request. These deposits will irrevocably and without restriction or condition be available to the public upon issuance of a patent. However, it should be understood that the availability of a deposit does not constitute a license to practice the subject invention in derogation of patent rights granted by government action.

The strains indicated below were deposited on Aug. 6, 2005 with the Agricultural Research Service (ARS) Culture Collection, housed in the Microbial Genomics and Bioprocessing Research Unit of the National Center for Agricultural Utilization Research (NCAUR), under the Budapest Treaty provisions. The strains were given the indicated accession numbers. The address of NCAUR is 1815 N. University Street, Peoria, Ill., 61604. During the pendency of this application, access to these deposits will be afforded to the Commissioner of Patents and Trademarks upon request. The deposits will irrevocably and without restriction or condition be available to the public upon issuance of a patent. However, it should be understood that the availability of a deposit does not constitute a license to practice the subject invention in derogation of patent rights granted by government action:

*Lactobacillus brevis* LB1154, ARS Accession No. NRRL B-30865;

*Lactobacillus buchneri* LN4888, ARS Accession No. NRRL B-30866;

*Lactobacillus reuteri* LR4933, ARS Accession No. NRRL B-30867;

*Lactobacillus crispatus* LI2127, ARS Accession No. NRRL B-30868;

*Lactobacillus crispatus* LI2350, ARS Accession No. NRRL B-30869;

*Lactobacillus crispatus* LI2366, ARS Accession No. NRRL B-30870.

The strain indicated below was deposited on Aug. 16, 2005 with the Agricultural Research Service (ARS) Culture Collection, housed in the Microbial Genomics and Bioprocessing Research Unit of the National Center for Agricultural Utilization Research (NCAUR), under the Budapest Treaty provisions. The strain was given the indicated accession number. The address of NCAUR is 1815 N. University Street, Peoria, Ill., 61604. During the pendency of this application, access to this deposit will be afforded to the Commissioner of Patents and Trademarks upon request. The deposit will irrevocably and without restriction or condition be available to the public upon issuance of a patent. However, it should be understood that the availability of a deposit does not constitute a license to practice the subject invention in derogation of patent rights granted by government action:

*Lactobacillus* species unknown UL3050, ARS Accession No. NRRL B-30871.

A method for treating pre-ensiled plant material to enhance the digestibility of the resulting silage by adding to the pre-ensiled plant material a digestibility enhancing amount of a composition containing a ferulate esterase producing bacterial strain or a functional mutant thereof of is also disclosed. Suitable pre-ensiled plant materials include grasses, maize, alfalfa and other legumes, wheat, sorghum, sunflower, barley and mixtures thereof.

An embodiment of the invention is a method for enhancing plant fiber digestion in an animal by feeding an effective amount of a ferulate esterase-containing composition to the animal, wherein the ferulate esterase is derived from a ferulate esterase producing bacterial strain or a functional mutant thereof. Suitable ferulate esterase producing bacterial strains or functional mutants thereof include Lactobacillus strains. Suitable *Lactobacillus* strains include *Lactobacillus buchneri* or functional mutant thereof, *Lactobacillus plantarum* or functional mutant thereof, *Lactobacillus brevis* or functional mutant thereof, *Lactobacillus reuteri* or functional mutant thereof, *Lactobacillus alimentarius* or functional mutant thereof, *Lactobacillus crispatus* or functional mutant thereof, and *Lactobacillus paralimentarius* or functional mutant thereof. Suitable *Lactobacillus buchneri* or functional mutant thereof, *Lactobacillus plantarum* or functional mutant thereof, *Lactobacillus brevis* or functional mutant thereof, *Lactobacillus reuteri* or functional mutant thereof, *Lactobacillus alimentarius* or functional mutant thereof, *Lactobacillus crispatus* or functional mutant thereof, and *Lactobacillus paralimentarius* or functional mutant thereof include *Lactobacillus buchneri*, strain LN4017, deposited as Patent Deposit No. PTA-6138, *Lactobacillus plantarum*, strain LP678, deposited as Patent Deposit No. PTA-6134, *Lactobacillus plantarum*, strain LP3710, deposited as Patent Deposit No. PTA-6136, *Lactobacillus plantarum*, strain LP3779, deposited as Patent Deposit No. PTA-6137, *Lactobacillus plantarum*, strain LP7109, deposited as Patent Deposit No. PTA-6139, *Lactobacillus brevis*, strain LB1154, deposited as Patent Deposit NRRL B-30865, *Lactobacillus buchneri*, strain LN4888, deposited as Patent Deposit NRRL B-30866, *Lactobacillus reuteri*, strain LR4933, deposited as Patent Deposit NRRL B-30867, Lactobacillus crispatus, strain LI2127, deposited as Patent Deposit NRRL B-30868, Lactobacillus crispatus, strain LI2350, deposited as Patent Deposit NRRL B-30869, *Lactobacillus crispatus*, strain LI2366, deposited as Patent Deposit NRRL B-30870, *Lactobacillus* species unknown, strain UL3050, deposited as Patent Deposit NRRL B-30871, and mixtures thereof.

The composition that is fed to the animal has been treated with an effective catalytic amount of the ferulate esterase producing bacterial strain or functional mutant thereof as is readily determinable by those skilled in the art in animal husbandry. Animals that are benefited by embodiments of the present invention are mammals and birds, including but not limited to ruminant, equine, bovine, porcine, caprine, ovine and avian species, e.g., poultry.

A further embodiment of the invention is a composition for use as a silage inoculant comprising a silage digestibility enhancing amount of *Lactobacillus paracasei tolerans*, strain LC3200, deposited as Patent Deposit No. PTA-6135 or a functional mutant thereof, a ferulate esterase producing bacterial strain or a functional mutant thereof, and a suitable carrier. Suitable ferulate esterase producing bacterial strains or functional mutants thereof include *Lactobacillus* strains. Suitable ferulate esterase producing *Lactobacillus* strains or functional mutants thereof include *Lactobacillus buchneri* or functional mutant thereof, *Lactobacillus plantarum* or functional mutant thereof, *Lactobacillus brevis* or functional mutant thereof, *Lactobacillus reuteri* or functional mutant thereof, *Lactobacillus alimentarius* or functional mutant thereof, *Lactobacillus crispatus* or functional mutant thereof, and *Lactobacillus paralimentarius* or functional mutant thereof. Suitable ferulate esterase producing *Lactobacillus buchneri* or functional mutant thereof, *Lactobacillus plantarum* or functional mutant thereof, *Lactobacillus brevis* or functional mutant thereof, *Lactobacillus reuteri* or functional mutant thereof, *Lactobacillus alimentarius* or functional mutant thereof, *Lactobacillus crispatus* or functional mutant thereof, and *Lactobacillus paralimentarius* or functional mutant thereof include *Lactobacillus buchneri*, strain LN4017, deposited as Patent Deposit No. PTA-6138, *Lactobacillus plantarum*, strain LP678, deposited as Patent Deposit No. PTA-6134, *Lactobacillus plantarum*, strain LP3710, deposited as Patent Deposit No. PTA-6136, *Lactobacillus plantarum*, strain LP3779, deposited as Patent Deposit No. PTA-6137, *Lactobacillus plantarum*, strain LP7109, deposited as Patent Deposit No. PTA-6139, *Lactobacillus brevis*, strain LB1154, deposited as Patent Deposit NRRL B-30865, *Lactobacillus buchneri*, strain LN4888, deposited as Patent Deposit NRRL B-30866, *Lactobacillus reuteri*, strain LR4933, deposited as Patent Deposit NRRL B-30867, *Lactobacillus crispatus*, strain LI2127, deposited as Patent Deposit NRRL B-30868, *Lactobacillus crispatus*, strain LI2350, deposited as Patent Deposit NRRL B-30869, *Lactobacillus crispatus*, strain LI2366, deposited as Patent Deposit NRRL B-30870, Lactobacillus species unknown, strain UL3050, deposited as Patent Deposit NRRL B-30871, and mixtures thereof.

In an embodiment of the invention the composition contains from about $10^1$ to about $10^{10}$ viable organisms of *Lactobacillus paracasei tolerans*, strain LC3200 or functional mutant thereof per gram of a pre-ensiled plant material and from about $10^1$ to about $10^{10}$ viable organisms of the ferulate esterase producing bacterial strain or functional mutant thereof per gram of a pre-ensiled plant material. In a further embodiment of the invention the composition contains from about $10^2$ to about $10^7$ viable organisms of *Lactobacillus paracasei tolerans*, strain LC3200 or functional mutant thereof per gram of a pre-ensiled plant material and from about $10^2$ to about $10^7$ viable organisms of the ferulate esterase producing bacterial strain or functional mutant thereof per gram of a pre-ensiled plant material. In yet a further embodiment of the invention the composition contains from about $10^3$ to about $10^6$ viable organisms of *Lactobacillus paracasei tolerans*, strain LC3200 or functional mutant thereof per gram of a pre-ensiled plant material and from about $10^3$ to about $10^6$ viable organisms of the ferulate esterase producing bacterial strain or functional mutant thereof per gram of a pre-ensiled plant material.

An embodiment of the invention is a substantially purified strain of a bacterium selected from the group consisting of *Lactobacillus buchneri*, strain LN4017, deposited as Patent Deposit No. PTA-6138, *Lactobacillus plantarum*, strain LP678, deposited as Patent Deposit No. PTA-6134, *Lactobacillus plantarum*, strain LP3710, deposited as Patent Deposit No. PTA-6136, *Lactobacillus plantarum*, strain LP3779, deposited as Patent Deposit No. PTA-6137, *Lactobacillus plantarum*, strain LP7109, deposited as Patent Deposit No. PTA-6139, *Lactobacillus paracasei tolerans*, strain LC3200 having ATCC Accession No. PTA-6135, *Lactobacillus brevis*, strain LB1154, deposited as Patent Deposit NRRL B-30865, *Lactobacillus buchneri*, strain LN4888, deposited as Patent Deposit NRRL B-30866, *Lactobacillus reuteri*, strain LR4933, deposited as Patent Deposit NRRL B-30867, *Lactobacillus crispatus*, strain LI2127, deposited as Patent Deposit NRRL B-30868, *Lactobacillus crispatus*, strain LI2350, deposited as Patent Deposit NRRL B-30869, *Lactobacillus crispatus*, strain LI2366, deposited as Patent Deposit NRRL B-30870, *Lactobacillus* species unknown, strain UL3050, deposited as Patent Deposit NRRL B-30871, and mixtures thereof.

In a further embodiment of the invention *Lactobacillus paracasei tolerans*, strain LC3200 in combination with *Lactobacillus buchneri* strain LN4017 not only enhances plant fiber digestion in animals but the combination also enhances the preservation of the ensiled forage by improving both the fermentation and aerobic stability of the silage. In a further embodiment of the invention *Lactobacillus paracasei tolerans*, strain LC3200 in combination with *Lactobacillus plantarum* strain LP3779 not only enhances plant fiber digestion in animals but the combination also enhances the preservation of the ensiled forage by improving the fermentation of the silage. In a further embodiment of the invention *Lactobacillus paracasei tolerans*, strain LC3200 in combination with *Lactobacillus plantarum* strain LP7109 not only enhances plant fiber digestion in animals but the combination also enhances the preservation of the ensiled forage by improving the fermentation of the silage. In another embodiment of the invention *Lactobacillus paracasei tolerans*, strain LC3200 in combination with *Lactobacillus buchneri* strain LN4017 and *Lactobacillus plantarum* strain LP7109 not only enhances plant fiber digestion in animals but the combination also enhances the preservation of the ensiled forage by improving both the fermentation and aerobic stability of the silage. Methods of using mixed cultures for improving either fermentation or aerobic stability of silage are disclosed in U.S. Pat. No. 6,403,804.

Embodiments of the present invention are further defined in the following Examples. It should be understood that these Examples, while indicating certain embodiments of the invention, are given by way of illustration only. From the above discussion and these Examples, one skilled in the art can ascertain the essential characteristics of this invention, and without departing from the spirit and scope thereof, can make various changes and modifications of the embodiments of the invention to adapt it to various usages and conditions. Thus, various modifications of the embodiments of the invention, in addition to those shown and described herein, will be apparent to those skilled in the art from the foregoing description. Such modifications are also intended to fall within the scope of the appended claims.

The disclosure of each reference set forth herein is incorporated herein by reference in its entirety.

Example 1

Effect of Silage Additives on Nutrient Digestibility in Lambs

Whole plant corn forage (WPCF) was harvested with a John Deere brand 3950 forage chopper, the theoretical chop length of the forage was ⅜ to ½ inch. The inoculant treatments *Lactobacillus paracasei tolerans* 3200 (LC3200) or *Lactobacillus buchneri* 4017 (LN4017), (LC3200 or LN4017) were grown and harvested by industry-accepted methods known in the art. The inoculant treatments were applied and mixed into the forage as a conveyor belt dropped the forage into the silos. The treatments were applied in the soluble form to supply $10^5$ colony forming units/gram (cfu/g) of forage for both inoculant treatments. A person walking over the top of each silo as it was filled packed the silos to a similar density. The silos were sealed with a layer of plastic and a plywood lid weighted with a 500 lb concrete weight was applied to each silo.

The test diet fed to lambs consisted of 90% whole plant corn silage (WPCS) and 10% supplement (42% protein soybean meal) on a dry matter (DM) basis, and was fed twice daily.

The digestion study was conducted with feeder lambs averaging in weight of approximately 50-70 lb. Twelve wether lambs were assigned by weight to each treatment; diet intake was set at 1.5× maintenance. A diet adjustment period was run for 7 days followed by a 5-day collection period. This was repeated to increase the number of treatment repetitions. Silage samples were composited on a daily basis by treatment. Feces and urine were collected daily and composited by lamb.

Silage samples taken periodically during the feeding study were evaluated for DM, pH, total nitrogen, neutral detergent fiber (NDF), acid detergent fiber (ADF), lactic acid and volatile fatty acid (VFA) concentrations.

The silages were all well fermented as illustrated by the low pH and the high concentrations of lactic acid as shown in Table 1. The pH value of forage inoculated with homofermentative strain LC3200 at ensilage was lower than that of the control and LN4017 treatments. Accordingly, the LC3200 treatment had a higher lactic acid concentration and a higher dry matter recovery than untreated or LN4017 treated silage and these observations were consistent with known effects of efficacious homofermentative silage inoculants.

TABLE 1

DM, silage chemical composition (% DM) and pH

| Item[1] | Control | LC3200 | LN4017 |
|---|---|---|---|
| Dry matter | 28.7 | 29.1 | 28.8 |
| DM recovery | 89.5 | 92.2 | 89.8 |
| pH | 3.63 | 3.54 | 3.62 |
| Lactic acid | 5.23 | 6.10 | 5.57 |
| Acetic acid | 1.83 | 1.43 | 2.03 |
| Propionic acid | 0.02 | 0.03 | nd |
| Butyric acid | nd | nd | nd |
| Isobutyric acid | 0.23 | 0.15 | 0.26 |
| Total nitrogen | 1.21 | 1.18 | 1.22 |
| NDF | 42.5 | 42.9 | 43.7 |
| ADF | 27.9 | 28.6 | 28.8 |

[1]Values expressed as least squares means.
nd = not detected

As shown in Table 2, inoculants increased DM and N digestibility when compared to the control (uninoculated) forage. Digestibility coefficients for NDF and ADF were higher in inoculated forages when compared to the control. In particular, LN4017 increased NDF digestibility by 4.3 percentage points (or 8.7%) and ADF digestibility by 6.3% points (or 13%).

TABLE 2

Lamb digestion trial results

| Item[1] | Control | LC3200 | LN4017 |
|---|---|---|---|
| Number of animals | 12 | 12 | 12 |
| Animal weight, lb | 69.1 | 67.7 | 68.9 |
| Dry matter intake, g/d | 557 | 541 | 545 |
| Digestibility, % | | | |
| Dry matter | 67.9 | 69.1 | 69.4 |
| Nitrogen | 67.8 | 69.7 | 69.9 |
| NDF | 49.2 | 51.7 | 53.5 |
| ADF | 46.7 | 49.9 | 53.0 |

[1]Values expressed as least squares means.

Example 2

Effect of Silage Additives on Nutrient Digestibility in Lambs

Whole plant corn forage (WPCF) was harvested with a John Deere brand 3950 forage chopper, theoretical chop length was ⅜ to ½ inch. The corn was harvested at approximately ⅔ milk line. The treatments were untreated silage (Control), and silage treated with *Lactobacillus paracasei tolerans* 3200 (LC3200) or *Lactobacillus buchneri* 4017 (LN4017), both applied at a rate of $1\times10^5$ cfu/g forage. The corn forage was blown into a John Deere brand forage wagon. The treatments were applied in the soluble form to the forage as the forage was dropped into the silo by conveyor. The silos were packed by having a person walk over the top of the forage as it was loaded into the silo. The silos were sealed with a layer of plastic and a plywood lid weighted with a 500 lb concrete weight.

Samples for nutrient analysis were taken from each silo as it was fed out for the lamb digestion study. These results are shown in Table 3.

TABLE 3

Final silage chemistries

| Item[1] | Control | LC3200 | LN4017 |
|---|---|---|---|
| Dry matter, % | 37.19 | 36.98 | 35.67 |
| PH | 3.8 | 3.8 | 3.7 |
| Dry matter recovery, % | 99.75 | 97.78 | 96.11 |
| % DM | | | |
| Total nitrogen | 1.16 | 1.15 | 1.21 |
| NDF | 36.55 | 36.74 | 36.44 |
| ADF | 19.31 | 19.04 | 19.47 |
| Lactic acid | 4.01 | 4.33 | 4.16 |
| Acetic acid | 0.74 | 0.81 | 1.26 |
| Propionic acid | 0.01 | 0.01 | 0.01 |
| Butyric acid | 0.01 | 0.01 | 0.01 |
| Isobutyric acid | 0.01 | 0.01 | 0.01 |

[1]Values expressed as least squares means.

A digestion study was conducted with twelve feeder lambs with an average weight of approximately 70 lb. Twelve wether lambs were assigned by weight to each treatment.

Intake was set at 1.2× the maintenance requirement for each lamb. The ration was fed twice daily and consisted of 90% corn silage and 10% supplement (42% protein soybean meal) on a dry matter basis as shown in Table 4.

TABLE 4

Ration chemistries

| Item[1] | Control | LC3200 | LN4017 |
|---|---|---|---|
| Dry matter, % | 39.57 | 39.08 | 37.61 |
| | | % DM | |
| Total nitrogen | 3.88 | 3.54 | 4.00 |
| NDF | 76.48 | 75.96 | 67.54 |
| ADF | 44.74 | 42.38 | 38.70 |

[1]Values expressed as least squares means.

The lambs were placed in metabolism crates, and a seven-day adaptation period was followed by a five-day collection period. The quantities fed were recorded. Refusals were collected, weighed and composited. A salt/mineral block was provided for each lamb and lambs had unlimited access to water. Silage samples were composited on a daily basis by treatment. Feces samples were composited on a daily basis by lamb. A percentage of the daily urine output was collected daily and composited by lamb.

Digestion coefficients are shown in Table 5. Nitrogen digestibility was higher for silage treated with LN4017 when compared with untreated silage (Control). ADF and NDF digestibility was higher for silage treated with LN4017 when compared to untreated silage (control).

TABLE 5

Lamb digestion trial results

| Item[1] | Control | LC3200 | LN4017 |
|---|---|---|---|
| Number of animals | 12 | 12 | 12 |
| Animal weight, lb | 70.6 | 70.5 | 70.2 |
| Dry matter intake, g/d | 2872 | 2833 | 2719 |
| Composition of diet | | | |
| Corn silage, DM % | 90 | 90 | 90 |
| Supplement, DM % | 10 | 10 | 10 |
| Digestibility, % | | | |
| Dry matter | 71.81 | 72.70 | 73.46 |
| Nitrogen | 45.89 | 49.55 | 52.48 |
| NDF | 53.86 | 56.41 | 57.53 |
| ADF | 43.84 | 44.51 | 46.50 |

[1]Values expressed as least squares means.

Example 3

Effect of Silage Additives on Nutrient Digestibility in Beef Steers

Whole plant corn forage (WPCF) was harvested with a John Deere brand 3950 forage chopper. The theoretical chop length of the forage was ⅜ to ½ inch. The corn was harvested at a moisture content of 66.66% and at approximately ⅔ milk line. Eighteen 2-ton silos were assigned to each treatment. The treatments were as follows: uninoculated silage (Control) and a combination of LC3200 applied at $2 \times 10^4$ cfu/g of forage and LN4017 applied at $1 \times 10^5$ cfu/g of forage (LC3200+LN4017). The corn forage was blown into a John Deere brand forage wagon.

The treatments were applied in the soluble form to the forage as the forage was dropped into the silo by conveyor. The silos were packed by having a person walk over the top of the forage as it was loaded into the silo. One silo from each treatment was filled from a wagonload of forage; filling order was alternated for every set of silos filled. The silos were sealed with a layer of plastic and a plywood lid weighted with a 500 lb concrete weight. Samples were taken from each silo for nutrient analysis as it was fed out for the steer performance study.

Forty (40) head of beef-type steers, averaging approximately 702 lb, were allotted by weight into two (2) treatments for a 56-day feeding study. Four (4) steers were assigned to a pen, with five pens randomly assigned to each treatment. The cattle were weighed at the start (days −1 and 0), middle (day 28) and end of the study (day 56). Steers were weighed following a 2-day shrink; the cattle were shrunk by cutting feed to 50% and removing water for 16 hours each day. Total gain and average daily gain were calculated for the entire feeding period.

Steers were fed twice daily via Calan™ gates. The Calan™ Gate System allowed for the feeding of animals on an individual basis by giving an animal access to only their assigned feeding stall. Animals were given access to fresh water and salt/mineral blocks at all times. The quantities fed were recorded and refusals were collected, weighed and composited, if needed. Samples of the ration were composited by week for dry matter determination to calculate dry matter intake.

Nutritional chemistries of the silage are shown in Table 6. Dry matter recovery was numerically higher for LN4017+LC3200 treated silages and this effect is consistent with the presence and activity of LC3200. Likewise acetic acid concentrations were higher in LN4017+LC3200 treated silages than in the control and this difference can be attributed to the activity of heterofermentative LN4017.

TABLE 6

Final silage chemistries

| Item[1] | Control | LC3200 + LN4017 |
|---|---|---|
| Dry matter, % | 31.94 | 31.94 |
| pH | 3.72 | 3.76 |
| Dry matter recovery, % | 92.88 | 94.13 |
| | % DM | |
| Total nitrogen | 1.23 | 1.36 |
| NDF | 42.77 | 41.22 |
| ADF | 27.62 | 25.86 |
| Lactic acid | 4.50 | 4.07 |
| Acetic acid | 1.15 | 1.83 |
| Propionic acid | nd | nd |
| Butyric acid | nd | nd |
| Isobutyric acid | nd | nd |
| Ammonia N | 13.03 | 13.01 |
| Ethanol | 1.22 | 1.10 | nd = not detectable
[1]Values expressed as least squares means.

Ration chemistries are shown in Table 7.

TABLE 7

Analyzed nutrient composition of diets fed to steers

| Item | Control | LC3200 + LN4017 |
|---|---|---|
| Dry matter, % | 34.36 | 33.94 |
| | % DM | |
| Total nitrogen | 1.85 | 1.97 |
| NDF | 36.39 | 36.43 |
| ADF | 23.31 | 25.90 |

Steer performance data is presented in Table 8. Weight gain/ton of ensued forage was approximately 12 lbs higher for steers fed silage inoculated with LC3200+LN4017 when compared to steers fed an uninoculated (Control) diet.

TABLE 8

Performance of steers fed test diets

| Item | Control | LC3200 + LN4017 |
|---|---|---|
| Number of animals | 20 | 20 |
| Days on test | 56 | 56 |
| Initial weight, lb | 704.6 | 701.1 |
| Final weight, lb | 861.8 | 868.4 |
| Average daily gain, lb | 2.81 | 2.99 |
| Feed efficiency | 5.74 | 5.25 |
| Dry matter intake, lb | 15.8 | 15.5 |
| % of Metabolic Intake | 87.6 | 85.6 |
| Silage dry matter, % | 31.94 | 31.94 |
| Composition of diet | | |
| WPCS silage, % of diet DM | 88.0 | 88.0 |
| Supplement, % of diet DM[1] | 12.0 | 12.0 |
| Dry matter recovery, % | 92.88 | 94.13 |
| Gain/ton WPCS silage fed, lb | 128.7 | 140.2 |
| Gain/ton forage ensiled, lb | 119.5 | 132.0 |

[1]Supplement 42/17 R200 contained: crude protein, 42% minimum with not more than 17% equivalent protein from non-protein nitrogen; crude fat, 1.25%; crude fiber, 5%; calcium, 5%; phosphorus, 1.5%; salt, 2.5%; potassium, 1.2%; vitamin A, 48,000 IU/lb; vitamin D, 4800 IU/lb; vitamin E, 48 IU/lb; Monensin, 200 g/ton.

Example 4

Effects of a Silage Additive on Fermentation and Aerobic Stability of Corn Silage Four (4) Pioneer® brand corn hybrids: 33P67, 34G13, 37B35 and 34G13 (Pioneer Hi-Bred International, Inc., Des Moines, Iowa) were harvested at respective dry matter values of 38.4, 32.1, 39.5, 31.8 and 36.0%, and ensiled with or without inoculation as experiments 1, 2, 3 and 4, respectively.

*Lactobacillus buchneri* strain LN4017 and *Lactobacillus paracasei tolerans* strain LC3200 were grown, stabilized and lyophilized as in known in the art. The treatments were control (untreated), LN4017 and LN4017+LC3200. LN4017 was applied to forage as an aqueous solution to deliver $1\times10^5$ CFU/g forage when applied at a rate of 2.2 mL/kg alone or in combination with LC3200. *Lactobacillus paracasei tolerans* strain LC3200 was use only in combination with LN4017 and applied to deliver $2\times10^4$ cfu/g when applied at a rate of 2.2 mL/kg. All treatments were applied by syringe dispersion via a 16-gauge needle, and thoroughly mixed into the forage by rolling on clean plastic sheeting.

For each treatment, 4 experimental 4"×14" polyvinyl chloride (PVC) pipe silos were filled and packed at 70% maximum packing density (approximately 160 kg DM $M^3$), using a hydraulic press. Experimental silos were fitted with rubber quick caps at each end, and the top cap was equipped with a Bunsen valve to allow gasses to escape.

Silos were opened after 50-57 days, emptied and the forage thoroughly mixed. Silage samples were allotted to the various analyses, namely: pH, dry matter and aerobic stability. Silage DM was determined by drying to a constant weight in a forced air oven at 62° C. Aerobic stability assessments were conducted on individual treatment replicates using the procedure of Honig (Proc. Of the Eurobac. Conf., P. Lingvall and S. Lindgren (ed.) (12-16 Aug. 1986) Swed. Univ. of Agric. Sci. Grass and Forage Report No. 3-1990. Pp. 76-81. Uppsala, Sweden.).

The time (h) for silage temperature to rise 1.7° C. above ambient was recorded (ROT). The integration of the area between the actual silage temperature curve and the line drawn by ambient temperature (Cumm-DD) was calculated.

Table 9 shows the effects of the inoculants on silage pH and aerobic stability at opening of the silos. Silages were well fermented as illustrated by the pH values, which ranged from 3.77-4.22 (Exp. 1), 3.81-3.90 (Exp. 2), 3.85-3.92 (Exp. 3) and 3.74-3.93 (Exp. 4). Inoculation with LN4017+LC3200 increased silage pH in Exp. 1, but had little or no effect on this parameter in any of the other experiments.

Control silages were relatively aerobically stable in Exp. 1 and Exp. 4 (values of 90 and 72 and, respectively) but unstable for the other 2 experiments (ROT values <33 h). LC3200+ LN4017 improved aerobic stability (ROT) by between 42 and 128 hours in all four (4) experiments. The combination of the *L. buchneri* strain LN4017 and *L. paracasei tolerans* strain LC3200 was on average numerically more effective at improving aerobic stability than inoculation with LN4017 alone. Cumm-DD values reflected ROT and therefore supported conclusions made using ROT regarding the stability of silages at opening.

Inoculation of WPC with inoculants containing ferulate esterase producing *Lactobacillus buchneri* strain LN4017 resulted in well fermented-silages, with an improved aerobic stability in all four (4) experiments. When compared to the control, the combination of LN4017 and LC3200 was numerically more effective at improving aerobic stability (by 42 to 128 h) than the LN4017 alone (by 3 to 90 h) demonstrating the presence of a positive interaction between LC3200 and LN4017.

TABLE 9

Effects of LN4017 + LC3200 on pH and aerobic stability of WPCS

| Treatment[1] | Experiment 1 | | | | Experiment 2 | | | | Experiment 3 | | | | Experiment 4 | | | |
|---|---|---|---|---|---|---|---|---|---|---|---|---|---|---|---|---|
| | pH | DM | ROT[2] | Cumm-DD[3] | pH | DM | ROT | Cumm-DD | pH | DM | ROT | Cumm-DD | pH | DM | ROT | Cumm-DD |
| Control | 3.81 | 33.6 | 90 | 68 | 3.89 | 31 | 21 | 76 | 3.88 | 39 | 32 | 83 | 3.86 | 32 | 72 | 70 |
| LN4017 | 3.93 | 31.9 | 134 | 13 | 3.85 | 33 | 24 | 7 | 3.88 | 37 | 78 | 14 | 3.84 | 32 | 129 | 17 |
| LN4017 + LC 3200 | 4.22 | 33.3 | 132 | 13 | 3.85 | 31 | 126 | 0 | 3.88 | 37 | 100 | 5 | 3.83 | 32 | 160 | 0 |

[1]Values are means of 4 experimental repetitions.
[2]Time in hours for silage to rise 1.7° C. above ambient.
[3]Integration of the area between the actual temperature curve and a line drawn by ambient temperature.

Example 5

Determination of Ferulate Esterase Activity

Lactic acid bacterial cultures, taken from Pioneer Hi-Bred's microbial culture collection, were grown in De Man Rogosa Sharpe broth (MRS broth; Difco™ Lactobacilli MRS; Becton Dickinson and Company, Sparks, Md. 21152 USA), prepared as described by the manufacturer, for 24 to 48 hours. The bacterial cells were harvested from MRS broth (10 mL) by centrifugation (3200×g; 20 minutes) and re-suspended in 1 mL of lysis buffer consisting of 100 mM HEPES (pH 7.0), sodium azide (10 µg/mL) and 5 µL of DNase (Roche Diagnostics corporation, Indianapolis, Ind.). The cells were lysed using a French Press (French Press Cell, Pressure, SIM-AMINCO Spectronic Instruments, Inc., Rochester, N.Y.) as is known in the art. These microbial cell lysates were then assayed for ferulate esterase activity as described below.

The substrate for ferulic acid esterase activity (4-nitrophenyl ferulic acid) was purchased from the Institute of Chemistry, Slovak Academy of Sciences Dubravska, Cesta 9, 845 38, Slovakia. Ferulate esterase activities of microbial cell lysates were determined using the assay described by Mastihuba et al. (2002, *Analytical Biochemistry* 309, 96-101) with modifications as detailed below.

The substrate was first dissolved in dimethylsulphoxide as described by Mastihuba et al. (2002, supra) and then diluted to the final working substrate solution of 2.5 mM in 0.5M $KPO_4$; pH 7.0. Eighty microliters (80 µL) of the substrate solution was dispensed into a 96 well microtiter plate containing twenty microliters (20 µL) of cell lysates prepared above and the solutions were thoroughly mixed and incubated at 37° C. for 30 minutes. Control wells consisting of substrate solution in buffer (2.5 mM in 0.5M $KPO_4$; pH 7.0) and cell lysates in buffer were included and otherwise treated the same way as the reaction mixtures. Following the incubation period, 20 µL from the reaction mixture or control wells was withdrawn using an 8-channel micropipette and added to a fresh microtiter plate well containing 180 µL of $KPO_4$ (pH 8). The final volume in each microtiter plate well was 200 µL. The solutions were mixed thoroughly and their optical densities determined at 405 nm using a microtiter plate reader (Vmax Kinetic Microplate Reader, Molecular Devices, Menlo Park Calif.). Reaction mixture absorbance readings were corrected for absorbance readings of controls prepared as described above. P-nitrophenol (0, 0.025, 0.05, 0.1, 0.15, 0.2 and 0.25 mM in 0.5 M $KPO_4$ (pH 8); 200 µL (Sigma Chemical Company, St Louis, Mo.; Cat #104-8) was used as a standard for the ferulate esterase assay. Protein concentrations of the cells were determined using Bradford reagent as is known in the art (Sigma Chemical Company., St Louis Mo.; Cat #B 6916; Bradford, M, (1976) Analytical Biochemistry 72 248-254). Ferulate esterase activities of the cell lysates were expressed as nanomoles of P-nitrophenyl (pNP) released per minute per mg of protein.

TABLE 10

Ferulate Esterase Activities of Lactic Acid Bacteria

| Strain Identification Number | FEA[1] (nanomoles pNP[2] released/mg protein/min.) |
|---|---|
| *Lactobacillus buchneri* strain LN4017 | 14.0 |
| *Lactobacillus buchneri* strain LN4888 | 23.0 |
| *Lactobacillus reuteri* strain LR4933 | 5.94 |
| *Lactobacillus brevis* strain LB1154 | 2.17 |
| *Lactobacillus crispatus* strain LI2127 | 10.1 |
| *Lactobacillus crispatus* strain LI 2366 | 7.77 |
| Unknown *Lactobacillus* strain UL3050 | 5.11 |
| *Lactobacillus crispatus* LI2350 | 6.86 |
| *Lactobacillus plantarum* strain 3710 | 2.68 |
| *Lactobacillus plantarum* strain 3779 | 2.26 |
| *Lactobacillus plantarum* strain 7109 | 1.69 |

[1]FEA, Ferulate Esterase Activity; data are means of 3 independent experiments.
[2]pNP, P-nitrophenol Ferulate esterase activities of lactic acid bacteria (Table 10) ranged from 1.69 to 23.0 nanomoles p-nitrophenol released per mg protein per minute.

Example 6

Effects of Inoculation with Ferulate Esterase Producing Lactic Acid Bacteria on pH and Digestibility of Rye Grass Silage Dry Matter and Fiber Ryegrass was the first spring cutting, harvested at the Pioneer Livestock Nutrition Center (PLNC), Sheldahl, Iowa in June 2005. The test strains were either grown and freeze dried by a contract manufacturer of Pioneer Hi-Bred International, Inc. or used as 24-48 hour fresh cultures grown on MRS broth as is known in the art. The test strains were all ferulate esterase producing bacteria as determined by pNP-ferulic acid method (see Example 5, Table 10).

The effects of inoculation with ferulate esterase producing *Lactobacillus crispatus* strain LI2127, *Lactobacillus crispatus* strain LI2350, unknown *Lactobacillus* strain UL3050, *Lactobacillus crispatus* strain LI2366; *Lactobacillus brevis* strain LB1154; *Lactobacillus buchneri* strains LN4017 and LN4888; and *Lactobacillus reuteri* strain LR4933 on rye grass silage dry matter and neutral detergent fiber digestion (DMD and NDFD, respectively) were determined.

The ryegrass was either left uninoculated (control) or inoculated with the test strains as described herein previously. All test strains were applied to forage at an estimated rate of $1 \times 10^5$ cfu/g fresh weight. Additionally, all test strains were applied to forage as aqueous solutions (10 mL/4.54 Kg fresh forage weight) and thoroughly mixed with the forage in a 30 gallon plastic bag.

Forage, 1.36 Kg was ensiled, in triplicate for each treatment, in polyethylene packet silos which were vacuum packed and heat sealed as described by Dennis et al. (1999) (Page 87 In Proc XII Int. Silage Conf. Swedish Univ. of Agric. Sci. Uppsala, Sweden). The packet silos were incubated at room temperature, and after 30 days, the silos were opened, emptied and the forage thoroughly mixed to give a uniform mass. Aqueous extracts of the silage from each silo were prepared by diluting ten (10) grams in ninety (90) mL of sterile distilled water and agitating the mixture in a stomacher (Stomacher 400, Seward Limited, London, England) for 1 minute at the medium setting. Silage pH was determined on these extracts immediately following preparation of the extracts. Dry matter concentrations were determined by drying to a constant weight in a forced air oven at 62° C. A portion of the silage was dried to constant weight at 62° C. and ground to pass through a 6 mm screen for determination of in situ DMD and NDFD.

Ground silage (1.5 g), prepared as described above was weighed into tared micro in situ bags (5.5 cm by 5.5 cm; 40±15 microns; Ankom Technology Corp., Fairport, N.Y.), which were then sealed and reweighed as is known in the art. In situ DMD analysis was conducted by incubating the micro in situ bags containing the silage in to the rumens of three (3) ruminally fistulated steers which had been fed and adapted to a grass silage diet for 2 weeks prior to experimentation. For each silo, three (3) repetitions were incubated in each of the 3-ruminally fistulated steers for 48 hours; hence a total of 27 bags were incubated for each treatment. In situ analysis was conducted by hanging weighted bags in the rumen of the steers for 48 hours as is known in the art.

Neutral detergent fiber concentrations (NDF) of the silage were determined before and after the 48-hour ruminal incubation using the Ankom Fiber Analyzer (Ankom Technology Corp., Fairport, N.Y.). Digestion coefficients of NDF (%) were calculated as the difference in NDF weight before versus after ruminal incubation divided by the weight of NDF before ruminal incubation multiplied by 100.

TABLE 11

Effects of Inoculation with Ferulate Esterase Producing Lactic Acid Bacteria on Mean Rye Grass silage pH, and Digestibility Coefficients for DM and NDF[1] (DMD and NDFD, respectively).

| Treatment | Silage pH | DMD[2] (% DM) | NDFD[3] (% NDF) |
|---|---|---|---|
| CONTROL | 4.55 | 61.0 | 52.5 |
| L. brevis LB1154 | 4.35 | 64.8 | 58.3 |
| L. buchneri LN4017 | 4.72 | 61.1 | 57.5 |
| L. buchneri LN4888 | 4.87 | 65.7 | 57.7 |
| L. reuteri LR4933 | 4.79 | 64.5 | 59.6 |
| L. crispatus LI2127 | 4.60 | 63.8 | 57.3 |
| L. crispatus LI2366 | 4.53 | 64.3 | 57.8 |
| L. crispatus LI2350 | 4.60 | 63.9 | 57.0 |
| Unknown Lactobacillus UL3050 | 4.11 | 63.9 | 56.6 |

[1]Values expressed are the mean of 3 silos per treatment.
[2]Dry matter digestibility (DMD), % initial dry matter (DM).
[3]Neutral detergent fiber digestibility (NDFD), % of initial neutral detergent fiber.

At harvest, the forage had a pH of 6.67 and DM (% fresh weight) of 32.9%. Compared to the untreated silage (control), L. brevis strain LB1154 and the unknown Lactobacillus strain UL3050 resulted in silage with a lower pH. In contrast, L. buchneri strains LN4017 and LN4888; L. reuteri strain LR4933, and L. crispatus strains LI2350 and LI2127 resulted in silage that had an increased pH.

Ferulate esterase producing L. buchneri strains LN4017 and LN4888; L. reuteri strain LR4933 and L. brevis strain LB1154 resulted in silage with substantially increased NDFD values (Table 11), with increases of between 5 and 7 units (or 9.5 to 13.3%). Inoculation with ferulate esterase producing L. crispatus strains LI2127 and LI2366 increased NDFD (Table 11) by approximately 5 units (or 9.5%); L. crispatus strain LI2350 and unknown Lactobacillus strain UL3050 increased NDFD by 4.1 to 4.5% units (or 7.8 to 8.6%).

Example 7

Effect of Inoculation with a Combination of Lactic Acid Bacteria Containing a Ferulate Esterase Producing Lactic Acid Bacterium on Nutrient Digestibility by Lambs Ryegrass was mowed with a John Deere mower/conditioner and allowed to wilt to approximately 35% dry matter. The forage was harvested on the following day using a John Deere 3950 two-row pull-type forage chopper. The theoretical chop length was ⅜ to ½ inch. The treatments were untreated silage (Control) and the same forage inoculated with a combination strain inoculant consisting of L. plantarum 7109, L. paracasei tolerans LC 3200 and L. buchneri LN4017 ($2\times10^4/2\times10^4/1\times10^5$ cfu/g forage, respectively). The inoculant treatment was applied as an aqueous solution and mixed into the forage as forage dropped from a conveyor belt into the silos. A person walked on the top of each silo during the filling so as to pack the silos to a similar density. The silos were sealed with a layer of plastic; a concrete weight (500 lb) was applied to the top of each silo.

The test diet fed to lambs, 100% grass silage, was fed twice daily. The digestion study was conducted with feeder lambs with an average initial weight of approximately 85 lb. Wether lambs stratified by weight were assigned to each treatment; diet intake was limited to 1.2× maintenance. Following a diet adjustment period of 7 days, all feces were collected for 5 days. Silage samples were obtained each day. Feces and urine were collected daily and composited by lamb for the 5 day period.

Silage samples taken periodically during the feeding study were assayed for DM, pH, total nitrogen, neutral detergent fiber (NDF), and acid detergent fiber (ADF).

Digestion of NDF (NDFD) (Table 13) by lambs was greater for silage inoculated with LP7109/LC3200/LN4017 than for uninoculated control silage. Inoculation with LP7109/LC3200/LN4017 increased acid detergent fiber (ADF) digestion (ADFD) by 10% units (or 24%) when compared to the control silages.

TABLE 13

Effects of Inoculation with a Combination of Strains Containing a Ferulate Esterase Producing Lactic Acid Bacterium on Digestion of Grass Silage in Lambs

| Item | Control | LP7109/LC3200/LN4017 |
|---|---|---|
| Number of animals | 11 | 12 |
| Animal weight, lb | 82.5 | 84.4 |
| Dry matter intake, g/d | 700.1 | 703.7 |
| % DM | | |
| Analysis of diet[1] | | |
| Dry matter | 30.91 | 38.03 |
| Total nitrogen | 2.33 | 2.04 |
| NDF | 57.35 | 61.72 |
| ADF | 38.41 | 41.32 |
| Digestibility, %[2] | | |
| Dry matter | 57.03 | 59.86 |
| Nitrogen | 65.74 | 65.86 |
| NDF | 55.99 | 61.37 |
| ADF | 44.05 | 54.75 |

[1]Values used to calculate digestibility. Values are expressed as the average of five replicate samples.
[2]Values are expressed as least squares means Having illustrated and described the principles of the embodiments of the present invention, it should be apparent to persons skilled in the art that the embodiments of the invention can be modified in arrangement and detail without departing from such principles. We claim all modifications that are within the spirit and scope of the appended claims.

All publications and published patent documents cited in this specification are incorporated herein by reference to the same extent as if each individual publication or published patent document was specifically and individually indicated to be incorporated by reference.

What is claimed is:

1. A method for enhancing plant fiber digestion in an animal, said method comprising feeding to said animal an effective amount of a composition comprising a biologically pure culture of a ferulate esterase producing *Lactobacillus* strain and feed plant material, wherein said *Lactobacillus* strain is selected from the group consisting of *Lactobacillus buchneri*, strain LN4017, deposited as Patent Deposit No. PTA-6138, *Lactobacillus plantarum*, strain LP678, deposited as Patent Deposit No. PTA-6134, *Lactobacillus plantarum*, strain LP3710, deposited as Patent Deposit No. PTA-6136, *Lactobacillus plantarum*, strain LP3779, deposited as Patent Deposit No. PTA-6137, *Lactobacillus plantarum*, strain LP7109, deposited as Patent Deposit No. PTA-6139, *Lactobacillus brevis*, strain LB1154, deposited as Patent Deposit NRRL B-30865, *Lactobacillus buchneri*, strain LN4888, deposited as Patent Deposit NRRL B-30866, *Lactobacillus reuteri*, strain LR4933, deposited as Patent Deposit NRRL B-30867, *Lactobacillus crispatus*, strain LI2127, deposited as Patent Deposit NRRL B-30868, *Lactobacillus crispatus*, strain LI2350, deposited as Patent Deposit NRRL B-30869, *Lactobacillus crispatus*, strain LI2366, deposited as Patent Deposit NRRL B-30870, and mixtures thereof, wherein said composition comprises $10^1$ to $10^{10}$ viable organisms of said *Lactobacillus* strain per gram of said feed plant material.

2. The method of claim 1, wherein said feed plant material is selected from the group consisting of grasses, maize, alfalfa, wheat, legumes, sorghum, sunflower, barley, and mixtures thereof.

3. The method of claim 1 wherein said composition comprises from $10^2$ to $10^7$ viable organisms of said *Lactobacillus* strain per gram of said feed plant material.

4. The method of claim 1 wherein said composition comprises from $10^3$ to $10^6$ viable organisms of said *Lactobacillus* strain per gram of said feed plant material.

5. The method of claim 1, wherein the feed plant material is silage produced from a pre-ensiled plant material.

6. The method of claim 5, wherein said pre-ensiled plant material is selected from the group consisting of grasses, maize, alfalfa, wheat, legumes, sorghum, sunflower, barley, and mixtures thereof.

7. The method of claim 5 wherein said composition comprises from $10^2$ to $10^7$ viable organisms of said *Lactobacillus* strain per gram of said feed plant material.

8. The method of claim 5 wherein said composition comprises from $10^3$ to $10^6$ viable organisms of said *Lactobacillus* strain per gram of said feed plant material.

9. The method of claim 1, wherein the composition further comprises a suitable carrier.

* * * * *